(12) United States Patent
Johnson et al.

(10) Patent No.: US 10,239,052 B2
(45) Date of Patent: Mar. 26, 2019

(54) SYNTHESIS OF MOLECULAR SIEVES HAVING MWW FRAMEWORK STRUCTURE

(71) Applicant: ExxonMobil Chemical Patents Inc., Baytown, TX (US)

(72) Inventors: Ivy D. Johnson, Lawrenceville, NJ (US); Nadya A. Hrycenko, Clinton, NJ (US)

(73) Assignee: ExxonMobil Chemical Patents Inc., Baytown, TX (US)

( * ) Notice: Subject to any disclaimer, the term of this patent is extended or adjusted under 35 U.S.C. 154(b) by 0 days.

(21) Appl. No.: 15/032,099

(22) PCT Filed: Dec. 19, 2014

(86) PCT No.: PCT/US2014/071350
§ 371 (c)(1),
(2) Date: Apr. 26, 2016

(87) PCT Pub. No.: WO2015/112293
PCT Pub. Date: Jul. 30, 2015

(65) Prior Publication Data
US 2017/0043327 A1 Feb. 16, 2017

Related U.S. Application Data

(60) Provisional application No. 61/931,821, filed on Jan. 27, 2014.

(30) Foreign Application Priority Data

Mar. 19, 2014 (EP) .................................... 14160679

(51) Int. Cl.
*B01J 29/70* (2006.01)
*C01B 39/48* (2006.01)
(Continued)

(52) U.S. Cl.
CPC ......... *B01J 29/7038* (2013.01); *B01J 35/002* (2013.01); *C01B 39/48* (2013.01);
(Continued)

(58) Field of Classification Search
None
See application file for complete search history.

(56) References Cited

U.S. PATENT DOCUMENTS 4,439,409 A    3/1984 Puppe et al.
4,822,941 A *  4/1989 Baillargeon ........ C01B 33/2884
                                                208/135

(Continued)

FOREIGN PATENT DOCUMENTS

EP    0 293 032      7/1993
WO    97/17290      5/1997
(Continued)

OTHER PUBLICATIONS

Baerlocher et al., "*Atlas of Zeolite Framework Types*", Fifth Revised Edition, 2001.
(Continued)

*Primary Examiner* — Colin W. Slifka
(74) *Attorney, Agent, or Firm* — Darryl M. Tyus

(57) ABSTRACT

The present invention provides an improved method for making molecular sieves having MWW framework structure using precipitated aluminosilicates (PAS), and the use of molecular sieves so made in processes for catalytic conversion of hydrocarbon compounds.

18 Claims, 8 Drawing Sheets

Example 8 - MCM-49, 68 hrs @ 160°C

(51) Int. Cl.
*C07C 2/66* (2006.01)
*B01J 35/00* (2006.01)

(52) U.S. Cl.
CPC ............ *C07C 2/66* (2013.01); *C07C 2529/70* (2013.01); *Y02P 20/52* (2015.11)

(56) References Cited

U.S. PATENT DOCUMENTS

| | | | |
|---|---|---|---|
| 4,826,667 | A | 5/1989 | Zones et al. |
| 4,954,325 | A | 9/1990 | Rubin et al. |
| 5,236,575 | A | 8/1993 | Bennett et al. |
| 5,250,277 | A | 10/1993 | Kresge et al. |
| 5,350,722 | A * | 9/1994 | Joly ................ B01J 29/7034 423/328.1 |
| 5,362,697 | A | 11/1994 | Fung et al. |
| 5,453,554 | A | 9/1995 | Cheng et al. |
| 5,827,491 | A * | 10/1998 | Emerson ............. C01B 33/38 423/328.2 |
| 6,077,498 | A | 6/2000 | Diaz Cabañas et al. |
| 6,756,030 | B1 | 6/2004 | Rohde et al. |
| 7,326,401 | B2 | 2/2008 | Tatsumi et al. |
| 7,713,513 | B2 | 5/2010 | Jan et al. |
| 7,842,277 | B2 | 11/2010 | Roth et al. |
| 7,959,599 | B2 | 6/2011 | Matusch |
| 8,110,176 | B2 | 2/2012 | Roth et al. |
| 8,562,942 | B2 | 10/2013 | Archer et al. |
| 2014/0234207 | A1 | 8/2014 | Johnson et al. |

FOREIGN PATENT DOCUMENTS

| | | |
|---|---|---|
| WO | 2005/118476 | 12/2005 |
| WO | 2006/070073 | 7/2006 |
| WO | 2010/014406 | 2/2010 |
| WO | 2010/021795 | 2/2010 |
| WO | 2013/048636 | 4/2013 |

OTHER PUBLICATIONS

Wu et al., "*Effect of Aging with Ultrasound on the Synthesis of MCM-49 Zeolite*", Chinese Journal of Catalysis, vol. 27, Issue 5, May 2006, pp. 375-377.

* cited by examiner

Example 5 - MCM-56, 38 hrs @ 160°C

Example 8 - MCM-49, 68 hrs @ 160°C

SYNTHESIS OF MOLECULAR SIEVES HAVING MWW FRAMEWORK STRUCTURE

CROSS REFERENCE TO RELATED APPLICATIONS

The present application is a National Stage Application of International Application No. PCT/US2014/071350 filed Dec. 19, 2014, which claims priority to and the benefits of U.S. Ser. No. 61/931,821 filed on Jan. 27, 2014, and EP 14160679.8, filed on Mar. 19, 2014, the disclosures of which are hereby incorporated by reference herein in their entireties.

FIELD OF THE INVENTION

The present invention relates to an improved method for making molecular sieves having MWW framework structure, particularly, methods for making MWW framework molecular sieves using precipitated aluminosilicates (PAS), and the use of molecular sieves so made in processes for catalytic conversion of hydrocarbon compounds.

BACKGROUND OF THE INVENTION

Molecular sieves having a MWW framework structure are commonly referred to as a "MWW family molecular sieve material". As used herein, the term "MWW family molecular sieve material" includes one or more of:

(i) molecular sieves made from a common first degree crystalline building block unit cell, in which the unit cell has the MWW framework topology. (A unit cell is a spatial arrangement of atoms which if tiled in three-dimensional space describes the crystal structure. Such crystal structures are discussed in the "Atlas of Zeolite Framework Types", Fifth edition, 2001, the entire content of which is incorporated as reference);

(ii) molecular sieves made from a common second degree building block, being a 2-dimensional tiling of such MWW framework topology unit cells, forming a monolayer of one unit cell thickness, preferably one c-unit cell thickness;

(iii) molecular sieves made from common second degree building blocks, being layers of one or more than one unit cell thickness, wherein the layer of more than one unit cell thickness is made from stacking, packing, or binding at least two monolayers of one unit cell thickness. The stacking of such second degree building blocks can be in a regular fashion, an irregular fashion, a random fashion, or any combination thereof; and (iv) molecular sieves made by any regular or random 2-dimensional or 3-dimensional combination of unit cells having the MWW framework topology.

The MWW family molecular sieve materials are characterized by having an X-ray diffraction pattern including d-spacing maxima at 12.4±0.25, 3.57±0.07 and 3.42±0.07 Angstroms (either calcined or as-synthesized). The MWW family molecular sieve materials may also be characterized by having an X-ray diffraction pattern including d-spacing maxima at 12.4±0.25, 6.9±0.15, 3.57±0.07 and 3.42±0.07 Angstroms (either calcined or as-synthesized). The X-ray diffraction data used to characterize said molecular sieve are obtained by standard techniques using the K-alpha doublet of copper as the incident radiation and a diffractometer equipped with a scintillation counter and associated computer as the collection system. Materials that belong to the MWW family include, but not limited to, MCM-22 (described in U.S. Pat. No. 4,954,325); PSH-3 (described in U.S. Pat. No. 4,439,409); SSZ-25 (described in U.S. Pat. No. 4,826,667); ERB-1 (described in European Patent No. 0293032); ITQ-1 (described in U.S. Pat. No. 6,077,498); ITQ-2 (described in International Patent Publication No. WO97/17290); ITQ-30 (described in International Patent Publication No. WO2005118476); MCM-36 (described in U.S. Pat. No. 5,250,277); MCM-49 (described in U.S. Pat. No. 5,236,575); MCM-56 (described in U.S. Pat. Nos. 5,362,697, 5,827,491, and 5,453,554); EMM-10 (described in U.S. Pat. No. 8,110,176), EMM-10-P (described in U.S. Pat. No. 7,959,599), EMM-12 (described in International Patent Publication No. WO2010/021795), EMM-13 (described in International Patent Publication No. WO2010/014406), and an MCM-22 family material (described in U.S. Pat. No. 7,842,277). Also, UZM-8 (described in U.S. Pat. No. 6,756,030); and UZM-8HS (described in U.S. Pat. No. 7,713,513). The entire contents of said patents and applications are incorporated herein by reference.

It is to be appreciated that the MWW family molecular sieves described above are distinguished from conventional large pore zeolite alkylation catalysts, such as mordenite, in that the MWW family molecular sieve materials have 12-ring surface pockets which do not communicate with the 10-ring internal pore system of the molecular sieve.

The MWW family molecular sieves have been found to be useful in a variety of hydrocarbon conversion processes, and are especially valuable for use in a process for producing alkylaromatics, particularly ethylbenzene and cumene, or for use in a process for oligomerization of olefins, particularly for production of dimers, trimmers and tetramers of olefins, e.g., ethylene, propylene, butylene, or mixtures thereof.

There is a need to decrease crystallization times and to increase reactor throughput when synthesizing MWW family molecular sieve materials by currently available means. Prior efforts to decrease crystallization time and to increase throughput met with the problem of increased impurity formation.

According to the present invention, it has now unexpectedly been found that we can significantly avoid the above problems by the use of PAS in an improved method for synthesizing MWW family molecular sieve materials. This improved method provides a MWW family molecular sieve material product unencumbered by impurities, e.g., crystals of ferrierite, kenyaite, or other non-MWW family molecular sieve materials as identified by X-ray diffraction, with adjustment of the composition of the crystallization reaction mixture and control of the crystallization conditions, as detailed herein.

SUMMARY OF THE INVENTION

According to one aspect of the invention, there is provided a method of making a MWW family molecular sieve material comprising the steps of:

(a) preparing a reaction mixture comprising an alkali or an alkaline earth metal (M) cation, a precipitated aluminosilicate comprising a source of aluminum (Al) and a source of silicon (Si), a structure-directing agent (R) and water, said reaction mixture having a composition in terms of mole ratios within the following ranges:

$SiO_2/Al_2O_3 = 10$ to $600$;

$H_2O/SiO_2 = 5$ to $30$;

$OH^-/SiO_2 = 0.001$ to $2$;

$M/SiO_2 = 0.001$ to $2$;

$R/SiO_2 = 0.001$ to $0.5$;

(b) crystallizing said reaction mixture of step (a) under crystallization conditions of a temperature of from about 90° C. to about 175° C. and a time for less than 90 hours to form a resulting mixture comprising crystals of said MWW family molecular sieve material and less than about 10 wt. % of impurity crystals having non-MWW framework structure based on the total weight of said MWW family molecular sieve material in said reaction mixture, as identified by X-ray diffraction; and (c) recovering at least a portion of said crystals of said MWW family molecular sieve material from said resulting mixture of step (b) as an as-synthesized MWW family molecular sieve material having an X-ray diffraction pattern including d-spacing maxima at 12.4±0.25, 6.9±0.15, 3.57±0.07 and 3.42±0.07 Angstroms.

Preferably, said precipitated aluminosilicate is a precipitated sodium aluminosilicate.

In one or more embodiments, said as-synthesized MWW family molecular sieve material is thermally treated by heating at a temperature of from about 370° C. to about 925° C. for a time of from 1 minute to about 20 hours to form a calcined MWW family molecular sieve material.

In another embodiment, said composition of said reaction mixture in terms of mole ratios is within the following ranges:

$SiO_2/Al_2O_3$=15 to 50;

$H_2O/SiO_2$=5 to 30;

$OH^-/SiO_2$=0.01 to 0.3;

$M/SiO_2$=0.01 to 0.3;

$R/SiO_2$=0.001 to 0.5;

wherein said as-synthesized MWW family molecular sieve material has the X-ray diffraction pattern of as-synthesized MCM-22 molecular sieve shown in Table 1, herein.

In one or more embodiments, said as-synthesized MCM-22 molecular sieve is thermally treated by heating at a temperature of from about 370° C. to about 925° C. for a time of from 1 minute to about 20 hours to form a calcined MCM-22 molecular sieve having the X-ray diffraction pattern shown in Table 2, herein.

In another embodiment, said composition of said reaction mixture in terms of mole ratios is within the following ranges:

$SiO_2/Al_2O_3$=15 to 35;

$H_2O/SiO_2$=5 to 30;

$OH^-/SiO_2$=0.1 to 0.3;

$M/SiO_2$=0.08 to 0.3;

$R/SiO_2$=0.1 to 0.35;

wherein said as-synthesized MWW family molecular sieve material has the X-ray diffraction pattern of as-synthesized MCM-49 molecular sieve shown in Table 3, herein.

In one or more embodiments, said as-synthesized MCM-49 molecular sieve is thermally treated by heating at a temperature of from about 370° C. to about 925° C. for a time of from 1 minute to about 20 hours to form a calcined MCM-49 molecular sieve having the X-ray diffraction pattern shown in Table 4, herein.

In another embodiment, said composition of said reaction mixture in terms of mole ratios is within the following ranges:

$SiO_2/Al_2O_3$=15 to 25;

$H_2O/SiO_2$=5 to 30;

$OH^-/SiO_2$=0.10 to 0.15;

$M/SiO_2$=0.10 to 0.15;

$R/SiO_2$=0.1 to 0.2;

wherein said as-synthesized MWW family molecular sieve material has the X-ray diffraction pattern of as-synthesized MCM-56 molecular sieve shown in Table 5, herein.

In one or more embodiments, said as-synthesized MCM-56 molecular sieve is thermally treated by heating at a temperature of from about 370° C. to about 925° C. for a time of from 1 minute to about 20 hours to form a calcined MCM-56 molecular sieve having the X-ray diffraction pattern shown in Table 6, herein.

In another aspect, the invention relates to a process for converting feedstock comprising hydrocarbon compounds to conversion product which comprises contacting said feedstock at hydrocarbon compound conversion conditions with a catalyst composition made by the method of this invention. In one embodiment, the conversion product comprises oligomerized olefins. In another embodiment, said feedstock comprises an alkylatable aromatic compound, such as benzene, and an alkylating agent such as ethylene, propylene or combinations thereof, and said conversion product comprises monoalkylated aromatic compounds, such as ethylbenzene and cumene.

DETAILED DESCRIPTION OF THE INVENTION

Figure 1:
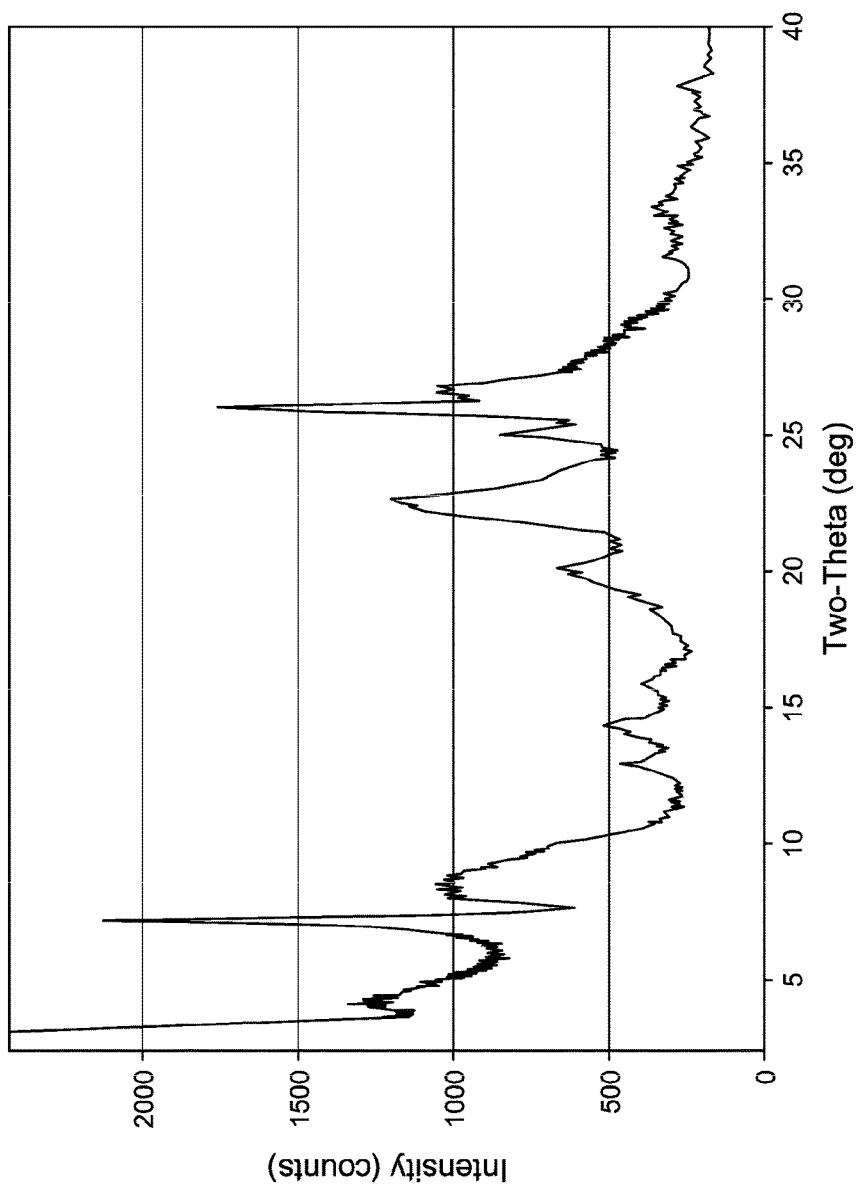
FIG. 1 shows the X-ray diffraction pattern of the as-synthesized MWW family molecular sieve material products of Example 1.

The porous crystalline MWW family molecular sieve material is made by the improved method of the present invention comprising the steps of:

(a) preparing a reaction mixture comprising an alkali or an alkaline earth metal (M) cation, a precipitated aluminosilicate comprising a source of aluminum (Al) and a source of silicon (Si), a structure-directing agent (R) and water, and optionally molecular sieve seed crystals, said reaction mixture having a composition in terms of mole ratios within the following ranges:

$SiO_2/Al_2O_3$=10 to 600, or 10 to 50, or 12 to 30;

$H_2O/SiO_2$=5 to 30, or 15 to 30, or 10 to 25;

$OH^-/SiO_2$=0.001 to 2, or 0.1 to 1;

$M/SiO_2$=0.001 to 2, or 0.1 to 1;

$R/SiO_2$=0.001 to 0.5, or 0.08 to 0.34;

(b) crystallizing said reaction mixture of step (a) under crystallization conditions of a temperature of from about 90° C. to about 175° C. and a time for less than 90 hours to form a resulting mixture comprising crystals of said MWW family molecular sieve material and less than about 10 wt. % of impurity crystals having non-MWW framework structure based on the total weight of said MWW family molecular sieve material in said reaction mixture, as identified by X-ray diffraction; and (c) recovering at least a portion of said crystals of said MWW family molecular sieve material from said resulting mixture of step (b) as an as-synthesized MWW family molecular sieve material having an X-ray diffraction pattern including d-spacing maxima at 12.4±0.25, 6.9±0.15, 3.57±0.07 and 3.42±0.07 Angstroms.

Preferably, said precipitated aluminosilicate is a precipitated sodium aluminosilicate.

The alkali metal or the alkaline earth metal (M) cation may optionally be incorporated into the precipitated aluminosilicate, such as, for example, in the form of a precipitated sodium aluminosilicate.

A calcined MWW family molecular sieve material is formed wherein said as-synthesized MWW family molecular sieve material is thermally treated by heating at a temperature of from about 370° C. to about 925° C. for a time of from 1 minute to about 20 hours.

In another embodiment, said as-synthesized MWW family molecular sieve material has the X-ray diffraction pattern of as-synthesized MCM-22 molecular sieve, wherein said composition of said reaction mixture in terms of mole ratios is within the following ranges:

$SiO_2/Al_2O_3$=10 to 60, or 15 to 50;

$H_2O/SiO_2$=5 to 30, or 10 to 25, or 5 to 15;

$OH^-/SiO_2$=0.01 to 0.5, or 0.01 to 0.3;

$M/SiO_2$=0.01 to 1, or 0.01 to 0.3;

$R/SiO_2$=0.001 to 0.5, or 0.01 to 0.34;

wherein the X-ray diffraction pattern of said as-synthesized MCM-22 molecular sieve is shown in Table 1:

TABLE 1

| Interplanar d-Spacing (Angstroms) | Relative Intensity $I/I_0 \times 100$ |
| --- | --- |
| 13.53 ± 0.2 | m-vs |
| 12.38 ± 0.2 | m-vs |
| 11.13 ± 0.2 | w-s |

TABLE 1-continued

| Interplanar d-Spacing (Angstroms) | Relative Intensity $I/I_0 \times 100$ |
| --- | --- |
| 9.15 ± 0.15 | w-s |
| 6.89 ± 0.15 | w-m |
| 4.47 ± 0.1 | w-m |
| 3.95 ± 0.08 | w-vs |
| 3.56 ± 0.06 | w-m |
| 3.43 ± 0.06 | m-vs |
| 3.36 ± 0.05 | w-s |

A calcined MCM-22 molecular sieve is formed, wherein said as-synthesized MCM-22 molecular sieve is thermally treated by heating at a temperature of from about 370° C. to about 925° C. for a time of from 1 minute to about 20 hours. The X-ray diffraction pattern of said calcined MCM-22 molecular sieve is shown in Table 2:

TABLE 2

| Interplanar d-Spacing (a) | Relative Intensity, $I/Io \times 100$ |
| --- | --- |
| 30.0 ± 2.2 | w-m |
| 2.21 ± 1.3 | w | more specifically, by the X-ray diffraction pattern shown in Table 3:

TABLE 3

| Interplanar d-Spacing (a) | Relative Intensity, $I/Io \times 100$ |
| --- | --- |
| 30.0 ± 2.2 | w-m |
| 22.1 ± 1.3 | w |
| 3.91 ± 0.07 | m-vs | and yet more specifically, by the X-ray diffraction pattern shown in Table 4:

TABLE 4

| Interplanar d-Spacing (Angstroms) | Relative Intensity $I/I_0 \times 100$ |
| --- | --- |
| 30.0 ± 2.2 | w-m |
| 22.1 ± 1.3 | w |
| 6.00 ± 0.10 | m-w |
| 4.64 ± 0.08 | w |
| 4.06 ± 0.07 | w-s |
| 3.91 ± 0.07 | w-vs |

In another embodiment, said as-synthesized MWW family molecular sieve material has the X-ray diffraction pattern of as-synthesized MCM-49 molecular sieve, wherein said composition of said reaction mixture in terms of mole ratios is within the following ranges:

$SiO_2/Al_2O_3$=19 to 35, or 15 to 35;

$H_2O/SiO_2$=5 to 30, or 10 to 25;

$OH^-/SiO_2$=0.1 to 0.3, or 0.1 to 0.15;

$M/SiO_2$=0.08 to 0.3, or 0.08 to 0.15;

$R/SiO_2$=0.1 to 0.35, or 0.15 to 0.35;

wherein the X-ray diffraction pattern of said as-synthesized MCM-49 molecular sieve is shown in Table 5:

TABLE 5

| Interplanar d-Spacing (Angstroms) | Relative Intensity $I/I_0 \times 100$ |
|---|---|
| 13.15 ± 0.26 | w-s* |
| 12.49 ± 0.24 | vs |
| 11.19 ± 0.22 | m-s |
| 6.43 ± 0.12 | w |
| 4.98 ± 0.10 | w |
| 4.69 ± 0.09 | w |
| 3.44 ± 0.07 | vs |
| 3.24 ± 0.06 | w |

*shoulder

A calcined MCM-49 molecular sieve is formed, wherein said as-synthesized MCM-49 molecular sieve is thermally treated by heating at a temperature of from about 370° C. to about 925° C. for a time of from 1 minute to about 20 hours. The X-ray diffraction pattern of said calcined MCM-49 molecular sieve is shown in Table 6:

TABLE 6

| Interplanar d-Spacing (Angstroms) | Relative Intensity $I/I_0 \times 100$ |
|---|---|
| 12.41 ± 0.24 | vs |
| 11.10 ± 0.22 | s |
| 8.89 ± 0.17 | m-s |
| 6.89 ± 0.13 | w |
| 6.19 ± 0.12 | m |
| 6.01 ± 0.12 | w |
| 5.56 ± 0.11 | w |
| 4.96 ± 0.10 | w |
| 4.67 ± 0.09 | w |
| 4.59 ± 0.09 | w |
| 4.39 ± 0.09 | w |
| 4.12 ± 0.08 | w |
| 4.07 ± 0.08 | w-m |
| 3.92 ± 0.08 | w-m |
| 3.75 ± 0.07 | w-m |
| 3.57 ± 0.07 | w |
| 3.43 ± 0.07 | s-vs |
| 3.31 ± 0.06 | w |
| 3.21 ± 0.06 | w |
| 3.12 ± 0.06 | w |
| 3.07 ± 0.06 | w |
| 2.83 ± 0.05 | w |
| 2.78 ± 0.05 | w |
| 2.69 ± 0.05 | w |
| 2.47 ± 0.05 | w |
| 2.42 ± 0.05 | w |
| 2.38 ± 0.05 | w |

In another embodiment, said as-synthesized MWW family molecular sieve material has the X-ray diffraction pattern of as-synthesized MCM-56 molecular sieve, wherein said composition of said reaction mixture in terms of mole ratios is within the following ranges:

$SiO_2/Al_2O_3$=15 to 25, or 15 to 20;

$H_2O/SiO_2$=5 to 30, or 10 to 25;

$OH^-/SiO_2$=0.05 to 0.2, or 0.10 to 0.15;

$M/SiO_2$=0.10 to 0.15, or 0.10 to 0.13;

$R/SiO_2$=0.08 to 0.3, or 0.1 to 0.2;

wherein the X-ray diffraction pattern of said as-synthesized MCM-56 molecular sieve is shown in Table 7:

TABLE 7

| Interplanar d-Spacing (Angstroms) | Relative Intensity $I/I_0 \times 100$ |
|---|---|
| 12.4 ± 0.2 | vs |
| 9.9 ± 0.3 | m |
| 6.9 ± 0.1 | w |
| 6.4 ± 0.3 | w |
| 6.2 ± 0.1 | w |
| 3.57 ± 0.07 | m-s |
| 3.44 ± 0.07 | vs |

A calcined MCM-56 molecular sieve is formed, wherein said as-synthesized MCM-56 molecular sieve is thermally treated by heating at a temperature of from about 370° C. to about 925° C. for a time of from 1 minute to about 20 hours. The X-ray diffraction pattern of said calcined MCM-56 molecular sieve is shown in Table 8:

TABLE 8

| Interplanar d-Spacing (Angstroms) | Relative Intensity $I/I_0 \times 100$ |
|---|---|
| 12.4 ± 0.2 | vs |
| 9.9 ± 0.3 | m |
| 6.9 ± 0.1 | w |
| 6.2 ± 0.1 | w |
| 3.55 ± 0.07 | m-s |
| 3.42 ± 0.07 | vs |

The X-ray diffraction data in Table 1 to Table 8 were collected with a Scintag diffraction system, equipped with a germanium solid state detector, using copper K-alpha radiation. The diffraction data were recorded by step-scanning at 0.02 degrees of two-theta (2θ), where theta (θ) is the Bragg angle, and a counting time of 10 seconds for each step. The interplanar spacings, d-spacings, were calculated in Angstrom units (Å), and the relative intensities of the lines, $I/I_o$ is one-hundredth of the intensity of the strongest line, above background, were derived with the use of a profile fitting routine (or second derivative algorithm). The intensities are uncorrected for Lorentz and polarization effects. The relative intensities are given in terms of the symbols vs=very strong (greater than 60-100), s=strong (greater than 40-60), m=medium (greater than 20-40) and w=weak (0-20). It should be understood that diffraction data listed as single lines may consist of multiple overlapping lines which under certain conditions, such as differences in crystallographic changes, may appear as resolved or partially resolved lines. Typically, crystallographic changes can include minor changes in unit cell parameters and/or a change in crystal symmetry, without a change in the structure. These minor effects, including changes in relative intensities, can also occur as a result of differences in cation content, framework composition, nature and degree of pore filling, and thermal and/or hydrothermal history. Other changes in diffraction patterns can be indicative of important differences between materials, which are the case for comparing MCM-22 with similar materials, e.g., MCM-49, MCM-56 and PSH-3.

In one or more embodiments, said reaction mixture of step (a) comprising said molecular sieve seed crystals is in an amount from greater than or equal to 0.05 wt. % to less than or equal to 5 wt. %, or in an amount from greater than or equal to 1 wt. % to less than or equal to 3 wt. %, based on the dry weight of said molecular sieve seed crystals divided by the sum of the dry weight of aluminum (Al) and the dry weight of silicon (Si) in said precipitated alumino silicate.

In one or more embodiments, said crystallization conditions of crystallizing step (b) include crystallizing said reaction mixture for said time of less than 40 hours, or from about 20 hours to about 75 hours.

In one or more embodiments, said molecular sieve seed crystals exhibit the X-ray diffraction pattern for an MWW family molecular sieve material.

In one or more embodiments, said MWW family molecular sieve material is selected from the group consisting of MCM-22, MCM-36, MCM-49, MCM-56, ITQ-1, ITQ-2, ITQ-30, PSH-3, SSZ-25, ERB-1, EMM-10, EMM-10-P, EMM-11, EMM-12, EMM-13, UZM-8 and UZM-8HS.

In one or more embodiments, said molecular sieve seed crystals exhibit said X-ray diffraction pattern for said MCM-56 crystals as set forth in Table 7 or Table 8.

In one or more embodiments, wherein said structure-directing agent (R) is selected from the group consisting of cyclopentylamine, cyclohexylamine, cycloheptylamine, hexamethyleneimine (HMI), heptamethyleneimine, homopiperazine, and combinations thereof.

In one or more embodiments, said M is sodium, and said R comprises hexamethyleneimine (HMI).

In one or more embodiments, said resulting mixture of step (c) comprises less than or equal to about 5 wt. % non-MWW impurity crystals, based on the total weight of said MWW crystals in said reaction mixture, as identified by X-ray diffraction.

In one or more embodiments, said impurity crystals having non-MWW framework structure is selected from the group consisting of ferrierite, kenyaite and mixtures thereof.

It is noted that the reaction mixture components can be supplied by more than one source. The reaction mixture can be prepared either batchwise or continuously.

Crystallization of the reaction mixture in step (b) of the present method is preferably carried out under stirred conditions in a suitable reactor vessel, such as for example, polypropylene containers or Teflon lined or stainless steel autoclaves. However, it is within the scope of this invention for crystallization to occur under static conditions.

The useful ranges of conditions for crystallization in this method are a temperature from about 90° C. to about 175° C., preferably, from about 90° C. to less than 160° C., e.g., from about 125° C. to about 175° C., and a time for less than 90 hours, preferably, for less than 40 hours, e.g., from about 20 to about 75 hours, preferably, at a stir rate of from about 40 to about 250 rpm, more preferably, from about 90 up to about 250 rpm, to form a resulting mixture comprising crystals of MWW family molecular sieve material and less than or equal to 10 wt. % impurity crystals having non-MWW framework structure based on the total weight of said MWW family molecular sieve material in said reaction mixture, as identified by X-ray diffraction. Thereafter, the crystals of as-synthesized MWW family molecular sieve material are separated from the resulting liquid mixture and recovered in step (c).

In one or more embodiments, said reaction mixture of step (b) is aged prior to crystallizing step (c) for from about 0.5 to about 48 hours, for example, from about 0.5 to about 24 hours, at a temperature of from about 25 to about 75° C. Preferably, the reaction mixture is aged with stirring at, for example, 50 rpm, for less than 48 hours at ambient temperature.

Not to be bound by any theory, it has been discovered that the use of precipitated aluminosiliates, with or without incorporated precipitated alkali or alkaline earth metal (M) cation, in the reaction mixture of the present invention permits a significant decrease in the $H_2O/SiO_2$ molar ratio of the reaction mixture with decreased crystallization time and increased reactor throughput while making the desired MWW family molecular sieve material with lowered amounts of impurity crystals having non-MWW framework structure.

A catalyst comprising said MWW family molecular sieve material made by the improved method herein may be used to effect conversion in chemical reactions, and is particularly useful in a process for selectively producing a desired monoalkylated aromatic compound comprising the step of contacting an alkylatable aromatic compound with an alkylating agent in the presence of the catalyst under at least partial liquid phase conditions. Another aspect of the present invention, therefore, is an improved alkylation catalyst comprising said synthetic, porous MWW family molecular sieve material made by the present improved method for use in a process for the selective production of monoalkyl benzene comprising the step of reacting benzene with an alkylating agent under alkylation conditions in the presence of said alkylation catalyst. Using the present catalyst to effect alkylation of an alkylatable aromatic compound, the alkylating agent may include an alkylating aliphatic group having 1 to 5 carbon atoms. The alkylating agent may be, for example, ethylene or propylene and the alkylatable aromatic compound in such an instance may suitably be benzene.

The MWW family molecular sieve material made by the improved method herein may be used as a catalyst component to effect hydrocarbon compound conversion, and is particularly useful as catalyst in a process for selectively producing a desired monoalkylated aromatic compound comprising the step of contacting an alkylatable aromatic compound with an alkylating agent under at least partial liquid phase conditions. For example, alkylation catalyst comprising the MWW family molecular sieve material made by the present improved method may be used in a process for the selective production of monoalkylated benzene comprising the step of reacting benzene with an alkylating agent such as, for example, ethylene or propylene, under alkylation conditions in the presence of said alkylation catalyst.

The term "aromatic" in reference to the alkylatable aromatic compounds which may be useful as feedstock in a process beneficially utilizing the present catalyst is to be understood in accordance with its art-recognized scope. This includes alkyl substituted and unsubstituted mono- and polynuclear compounds. Compounds of an aromatic character that possess a heteroatom are also useful provided they do not act as catalyst poisons under the reaction conditions selected.

Substituted aromatic compounds that can be alkylated herein must possess at least one hydrogen atom directly bonded to the aromatic nucleus. The aromatic rings can be substituted with one or more alkyl, aryl, alkaryl, alkoxy, aryloxy, cycloalkyl, halide, and/or other groups that do not interfere with the alkylation reaction.

Suitable aromatic compounds include benzene, naphthalene, anthracene, naphthacene, perylene, coronene, and phenanthrene, with benzene being preferred.

Generally, the alkyl groups that can be present as substituents on the aromatic compound contain from 1 to about 22 carbon atoms, and usually from about 1 to 8 carbon atoms, and most usually from about 1 to 4 carbon atoms.

Suitable alkyl substituted aromatic compounds include toluene, xylene, isopropylbenzene, n-propylbenzene, alpha-methylnaphthalene, ethylbenzene, mesitylene, durene, cymenes, butylbenzene, pseudocumene, o-diethylbenzene, m-diethylbenzene, p-diethylbenzene, isoamylbenzene, isohexylbenzene, pentaethylbenzene, pentamethylbenzene;

1,2,3,4-tetraethylbenzene; 1,2,3,5-tetramethylbenzene; 1,2,4-triethylbenzene; 1,2,3-trimethylbenzene, m-butyltoluene; p-butyltoluene; 3,5-diethyltoluene; o-ethyltoluene; p-ethyltoluene; m-propyltoluene; 4-ethyl-m-xylene; dimethylnaphthalenes; ethylnaphthalene; 2,3-dimethylanthracene; 9-ethylanthracene; 2-methylanthracene; o-methylanthracene; 9,10-dimethylphenanthrene; and 3-methyl-phenanthrene. Higher molecular weight alkylaromatic compounds can also be used as starting materials and include aromatic hydrocarbons such as are produced by the alkylation of aromatic hydrocarbons with olefin oligomers. Such products are frequently referred to in the art as alkylate and include hexylbenzene, nonylbenzene, dodecylbenzene, pentadecylbenzene, hexyltoluene, nonyltoluene, dodecyltoluene, pentadecyltoluene, etc. Very often alkylate is obtained as a high boiling fraction in which the alkyl group attached to the aromatic nucleus varies in size from about $C_6$ to about $C_{12}$. When cumene or ethylbenzene is the desired product, the present process produces acceptably little by-products such as xylenes. The xylenes made in such instances may be less than about 500 ppm.

Reformate containing a mixture of benzene, toluene and/or xylene constitutes a useful feed for the alkylation process of this invention.

The alkylating agents which are useful as feedstock in a process beneficially utilizing the catalyst of this invention generally include any aliphatic or aromatic organic compound having one or more available alkylating aliphatic groups capable of reaction with the alkylatable aromatic compound, preferably, with the alkylating group possessing from 1 to 5 carbon atoms. Examples of suitable alkylating agents are olefins such as ethylene, propylene, the butenes, and the pentenes; alcohols (inclusive of monoalcohols, dialcohols, trialcohols, etc.) such as methanol, ethanol, the propanols, the butanols, and the pentanols; aldehydes such as formaldehyde, acetaldehyde, propionaldehyde, butyraldehyde, and n-valeraldehyde; and alkyl halides such as methyl chloride, ethyl chloride, the propyl chlorides, the butyl chlorides, and the pentyl chlorides, and so forth.

Mixtures of light olefins are useful as alkylating agents in the alkylation process utilizing the catalyst of this invention. Also, such mixtures of light olefins are useful as reactants in the oligomerization process utilizing the catalyst of this invention. Accordingly, mixtures of ethylene, propylene, butenes, and/or pentenes which are major constituents of a variety of refinery streams, e.g., fuel gas, gas plant off-gas containing ethylene, propylene, etc., naphtha cracker off-gas containing light olefins, refinery FCC propane/propylene streams, etc., are useful alkylating agents and oligomerization reactants herein. For example, a typical FCC light olefin stream possesses the following composition in Table 9:

TABLE 9

|  | Wt. % | Mole % |
| --- | --- | --- |
| Ethane | 3.3 | 5.1 |
| Ethylene | 0.7 | 1.2 |
| Propane | 4.5 | 15.3 |
| Propylene | 42.5 | 46.8 |
| Isobutane | 12.9 | 10.3 |
| n-Butane | 3.3 | 2.6 |
| Butenes | 22.1 | 18.32 |
| Pentanes | 0.7 | 0.4 |

For these uses of catalyst comprising the MWW family molecular sieve material made by the present method, products may include ethylbenzene from the reaction of benzene with ethylene, cumene from the reaction of benzene with propylene, ethyltoluene from the reaction of toluene with ethylene, cymenes from the reaction of toluene with propylene, and sec-butylbenzene from the reaction of benzene and n-butenes, a mixture of heavier olefins from the oligomerization of light olefins. Particularly preferred uses of this catalyst relate to the production of cumene by the alkylation of benzene with propylene, production of ethylbenzene by the alkylation of benzene with ethylene, and oligomerization of ethylene, propylene, butylene, or mixtures thereof.

The hydrocarbon compound conversion processes contemplated for use of this catalyst include, but are not limited to, oligomerization of olefins and may be conducted such that the reactants are brought into contact with the required catalyst in a suitable reaction zone such as, for example, in a flow reactor containing a fixed bed of the catalyst composition, under effective conversion conditions. Such conditions include a temperature of from about 0 to about 1000° C., preferably from about 0 to about 800° C., a pressure of from about 0.1 to about 1000 atmospheres, preferably from about 0.125 to about 500 atmospheres, and a feed weight hourly space velocity (WHSV) of from about 0.01 to 500 $hr^{-1}$, preferably from about 0.1 to about 100 $hr^{-1}$. If a batch reactor is used, the reaction time will be from about 1 minute to about 100 hours, preferably from about 1 hour to about 10 hours.

An alkylation process utilizing this catalyst may be conducted such that the reactants, i.e., the alkylatable aromatic compound and the alkylating agent, are brought into contact with the catalyst in a suitable reaction zone such as, for example, a flow reactor containing a fixed bed of the catalyst composition, under effective alkylation conditions. Such conditions include a temperature of from about 0 to about 500° C., preferably from about 10 to about 260° C., a pressure of from about 0.2 to about 250 atmospheres, preferably from about 1 to about 55 atmospheres, a molar ratio of alkylatable aromatic compound to alkylating agent of from about 0.1:1 to about 50:1, preferably from about 0.5:1 to about 10:1, and a feed weight hourly space velocity (WHSV) based on the alkylating agent of from about 0.1 to 500 $hr^{-1}$, preferably from about 0.5 to about 100 $hr^{-1}$.

The reactants can be in either the vapor phase or partially or completely in the liquid phase and can be neat, i.e., free from intentional admixture or dilution with other material, or they can be brought into contact with the alkylation catalyst composition with the aid of carrier gases or diluents such as, for example, hydrogen or nitrogen.

When benzene is alkylated with ethylene to produce ethylbenzene, the alkylation reaction is preferably carried out in the liquid phase under conditions including, a temperature of from about 150 to about 300° C., more preferably from about 170 to about 260° C.; a pressure up to about 204 atmospheres, more preferably from about 20 atmospheres to about 55 atmospheres; a weight hourly space velocity (WHSV) based on the ethylene alkylating agent of from about 0.1 to about 20 $hr^{-1}$, more preferably from about 0.5 to 6 $hr^{-1}$; and a ratio of benzene to ethylene in the alkylation reactor of from about 0.5:1 to about 100:1 molar, preferably from about 0.5:1 to about 30:1 molar, more preferably from about 1:1 to about 10:1 molar.

When benzene is alkylated with propylene to produce cumene, the reaction may also take place under liquid phase conditions including a temperature of up to about 250° C., preferably up to about 150° C., e.g., from about 10 to about 125° C.; a pressure of about 250 atmospheres or less, e.g., from about 1 to about 30 atmospheres; a weight hourly space velocity (WHSV) based on propylene alkylating agent of from about 0.1 hr$^{-1}$ to about 250 hr$^{-1}$, preferably from about 1 hr$^{-1}$ to about 50 hr$^{-1}$; and a ratio of benzene to propylene in the alkylation reactor of from about 0.5:1 to about 100:1 molar, preferably from about 0.5:1 to about 30:1 molar, more preferably from about 1:1 to about 10:1 molar.

The catalyst of the present invention may be used in a variety of forms. For certain applications of the catalyst, the average particle size of the crystalline molecular sieve component may be from about 0.05 to about 200 microns, for example, from 20 to 200 microns.

When used as catalyst for alkylation, the alkylation reactor effluent contains the excess aromatic feed, monoalkylated product, polyalkylated products, and various impurities. The aromatic feed is recovered by distillation and recycled to the alkylation reactor. Usually a small bleed is taken from the recycle stream to eliminate unreactive impurities from the loop. The bottoms from the distillation may be further distilled to separate monoalkylated product from polyalkylated products and other heavies.

The polyalkylated products separated from the alkylation reactor effluent may be reacted with additional aromatic feed in a transalkylation reactor, separate from the alkylation reactor, over a suitable transalkylation catalyst. The transalkylation catalyst may comprise one or a mixture of crystalline molecular sieves having the structure of zeolite Beta, zeolite Y (natural or synthetic forms), mordenite (natural and synthetic forms) or an MWW family molecular sieve material.

Zeolite Beta is disclosed in U.S. Pat. No. 3,308,069. Zeolite Y and mordenite occur naturally but may also be used in one of their synthetic forms, such as Ultrastable Y (USY), which is disclosed in U.S. Pat. No. 3,449,070, Rare-earth exchanged Y (REY), which is disclosed in U.S. Pat. No. 4,415,438, and TEA-mordenite (i.e., synthetic mordenite prepared from a reaction mixture comprising a tetraethylammonium directing agent), which is disclosed in U.S. Pat. Nos. 3,766,093 and 3,894,104. However, in the case of TEA-mordenite for use in the transalkylation catalyst, the particular synthesis regimes described in the patents noted lead to the production of a mordenite product composed of predominantly large crystals with a size greater than 1 micron and typically around 5 to 10 micron. It has been found that controlling the synthesis so that the resultant TEA-mordenite has an average crystal size of less than 0.5 micron results in a transalkylation catalyst with materially enhanced activity for liquid phase aromatics transalkylation.

The catalyst of the present invention may include an inorganic oxide material matrix or binder. Such matrix materials include synthetic or naturally occurring substances as well as inorganic materials such as clay, silica and/or metal oxides, e.g., alumina. The latter may be either naturally occurring or in the form of gelatinous precipitates or gels including mixtures of silica and metal oxides. Naturally occurring clays which can be composited with the inorganic oxide material include those of the montmorillonite and kaolin families, which families include the subbentonites and the kaolins commonly known as Dixie, McNamee, Georgia and Florida clays or others in which the main mineral constituent is halloysite, kaolinite, dickite, nacrite or anauxite. Such clays can be used in the raw state as originally mined or initially subjected to calcination, acid treatment or chemical modification.

Specific useful catalyst matrix or binder materials employed herein include silica, alumina, zirconia, titania, silica-alumina, silica-magnesia, silica-zirconia, silica-thoria, silica-beryllia, silica-titania, as well as, ternary compositions such as silica-alumina-thoria, silica-alumina-zirconia, silica-alumina-magnesia and silica-magnesia-zirconia. The matrix can be in the form of a cogel. A mixture of these components could also be used.

The relative proportions of crystalline molecular sieve and binder or matrix, if present, may vary widely with the crystalline molecular sieve content ranging from about 1 to about 99 percent by weight, and more usually in the range of about 30 to about 80 percent by weight of the total catalyst. Of course, the catalyst may comprise a self-bound molecular sieve or an unbound molecular sieve, thereby being about 100% crystalline molecular sieve MWW family molecular sieve material.

The catalyst of the present invention, or its crystalline molecular sieve component, may or may not contain added functionalization, such as, for example, a metal of Group VI (e.g., Cr and Mo), Group VII (e.g., Mn and Re) or Group VIII (e.g., Co, Ni, Pd and Pt), or phosphorus.

The invention is further disclosed in the following numbered embodiments:

Embodiment 1

A method of making a MWW family molecular sieve material comprising the steps of:
(a) preparing a reaction mixture comprising an alkali or an alkaline earth metal (M) cation, a precipitated aluminosilicate comprising a source of aluminum (Al) and a source of silicon (Si), a structure-directing agent (R) and water, said reaction mixture having a composition in terms of mole ratios within the following ranges:

$SiO_2/Al_2O_3$=10 to 600;

$H_2O/SiO_2$=5 to 30;

$OH^-/SiO_2$=0.001 to 2;

$M/SiO_2$=0.001 to 2;

$R/SiO_2$=0.001 to 0.5;

(b) crystallizing said reaction mixture of step (a) under crystallization conditions of a temperature of from about 90° C. to about 175° C. and a time for less than 90 hours to form a resulting mixture comprising crystals of said MWW family molecular sieve material and less than about 10 wt. % of impurity crystals having non-MWW framework structure based on the total weight of said MWW family molecular sieve material in said reaction mixture, as identified by X-ray diffraction; and
(c) recovering at least a portion of said crystals of said MWW family molecular sieve material from said resulting mixture of step (b) as an as-synthesized MWW family molecular sieve material having an X-ray diffraction pattern including d-spacing maxima at 12.4±0.25, 6.9±0.15, 3.57±0.07 and 3.42±0.07 Angstroms.

Embodiment 2

The method of embodiment 1, wherein said as-synthesized MWW family molecular sieve material is thermally treated by heating at a temperature of from about 370° C. to about 925° C. for a time of from 1 minute to about 20 hours to form a calcined MWW family molecular sieve material.

Embodiment 3

The method of any preceding embodiment, wherein said composition of said reaction mixture in terms of mole ratios is within the following ranges:

$SiO_2/Al_2O_3$=15 to 50;

$H_2O/SiO_2$=5 to 30;

$OH^-/SiO_2$=0.01 to 0.3;

$M/SiO_2$=0.01 to 0.3;

$R/SiO_2$=0.01 to 0.5;

wherein said as-synthesized MWW family molecular sieve material has the X-ray diffraction pattern of as-synthesized MCM-22 molecular sieve shown in Table 1:

TABLE 1

| Interplanar d-Spacing (Angstroms) | Relative Intensity $I/I_0 \times 100$ |
| --- | --- |
| 13.53 ± 0.2 | m-vs |
| 12.38 ± 0.2 | m-vs |
| 11.13 ± 0.2 | w-s |
| 9.15 ± 0.15 | w-s |
| 6.89 ± 0.15 | w-m |
| 4.47 ± 0.1 | w-m |
| 3.95 ± 0.08 | w-vs |
| 3.56 ± 0.06 | w-m |
| 3.43 ± 0.06 | m-vs |
| 3.36 ± 0.05 | w-s |

Embodiment 4

The method of embodiment 3, wherein said as-synthesized MCM-22 molecular sieve is thermally treated by heating at a temperature of from about 370° C. to about 925° C. for a time of from 1 minute to about 20 hours to form a calcined MCM-22 molecular sieve having the X-ray diffraction pattern shown in Table 2:

TABLE 2

| Interplanar d-Spacing (Angstroms) | Relative Intensity $I/I_0 \times 100$ |
| --- | --- |
| 30.0 ± 2.2 | w-m |
| 22.1 ± 1.3 | w |

Embodiment 5

The method of any preceding embodiment, wherein said composition of said reaction mixture in terms of mole ratios is within the following ranges:

$SiO_2/Al_2O_3$=15 to 35;

$H_2O/SiO_2$=5 to 30;

$OH^-/SiO_2$=0.1 to 0.3;

$M/SiO_2$=0.08 to 0.3;

$R/SiO_2$=0.10 to 0.35;

wherein said as-synthesized MWW family molecular sieve material has the X-ray diffraction pattern of as-synthesized MCM-49 molecular sieve shown in Table 5:

TABLE 5

| Interplanar d-Spacing (Angstroms) | Relative Intensity $I/I_0 \times 100$ |
| --- | --- |
| 13.15 ± 0.26 | w-s* |
| 12.49 ± 0.24 | vs |
| 11.19 ± 0.22 | m-s |
| 6.43 ± 0.12 | w |
| 4.98 ± 0.10 | w |
| 4.69 ± 0.09 | w |
| 3.44 ± 0.07 | vs |
| 3.24 ± 0.06 | w |

*shoulder

Embodiment 6

The method of embodiment 5, wherein said as-synthesized MCM-49 molecular sieve is thermally treated by heating at a temperature of from about 370° C. to about 925° C. for a time of from 1 minute to about 20 hours to form a calcined MCM-49 molecular sieve having the X-ray diffraction pattern shown in Table 6:

TABLE 6

| Interplanar d-Spacing (Angstroms) | Relative Intensity $I/I_0 \times 100$ |
| --- | --- |
| 12.41 ± 0.24 | vs |
| 11.10 ± 0.22 | s |
| 8.89 ± 0.17 | m-s |
| 6.89 ± 0.13 | w |
| 6.19 ± 0.12 | m |
| 6.01 ± 0.12 | w |
| 5.56 ± 0.11 | w |
| 4.96 ± 0.10 | w |
| 4.67 ± 0.09 | w |
| 4.59 ± 0.09 | w |
| 4.39 ± 0.09 | w |
| 4.12 ± 0.08 | w |
| 4.07 ± 0.08 | w-m |
| 3.92 ± 0.08 | w-m |
| 3.75 ± 0.07 | w-m |
| 3.57 ± 0.07 | w |
| 3.43 ± 0.07 | s-vs |
| 3.31 ± 0.06 | w |
| 3.21 ± 0.06 | w |
| 3.12 ± 0.06 | w |
| 3.07 ± 0.06 | w |
| 2.83 ± 0.05 | w |
| 2.78 ± 0.05 | w |
| 2.69 ± 0.05 | w |
| 2.47 ± 0.05 | w |
| 2.42 ± 0.05 | w |
| 2.38 ± 0.05 | w |

Embodiment 7

The method of embodiment 1, wherein said composition of said reaction mixture, in terms of mole ratios, is within the following ranges:

$SiO_2/Al_2O_3$=15 to 25;

$H_2O/SiO_2$=5 to 30;

$OH^-/SiO_2$=0.10 to 0.15;

$M/SiO_2$=0.10 to 0.15;

$R/SiO_2$=0.1 to 0.2;

wherein said as-synthesized MWW family molecular sieve material has the X-ray diffraction pattern of as-synthesized MCM-56 molecular sieve shown in Table 7:

TABLE 7

| Interplanar d-Spacing (Angstroms) | Relative Intensity $I/I_0 \times 100$ |
|---|---|
| 12.4 ± 0.2 | vs |
| 9.9 ± 0.3 | m |
| 6.9 ± 0.1 | w |
| 6.4 ± 0.3 | w |
| 6.2 ± 0.1 | w |
| 3.57 ± 0.07 | m-s |
| 3.44 ± 0.07 | vs |

Embodiment 8

The method of embodiment 7, wherein said as-synthesized MCM-56 molecular sieve is thermally treated by heating at a temperature of from about 370° C. to about 925° C. for a time of from 1 minute to about 20 hours to form a calcined MCM-56 molecular sieve having the X-ray diffraction pattern shown in Table 8:

TABLE 8

| Interplanar d-Spacing (Angstroms) | Relative Intensity $I/I_0 \times 100$ |
|---|---|
| 12.4 ± 0.2 | vs |
| 9.9 ± 0.3 | m |
| 6.9 ± 0.1 | w |
| 6.2 ± 0.1 | w |
| 3.55 ± 0.07 | m-s |
| 3.42 ± 0.07 | vs |

Embodiment 9

The method of any preceding embodiment, wherein said alkali or said alkaline earth metal (M) cation is incorporated into the precipitate aluminosilicate.

Embodiment 10

The method of any preceding embodiment, wherein said reaction mixture of step (a) further comprises molecular sieve seed crystals in an amount from greater than or equal to 0.05 wt. % to less than or equal to 5 wt. %, or in an amount from greater than or equal to 1 wt. % to less than or equal to 3 wt. %, based on the dry weight of said molecular sieve seed crystals divided by the sum of the dry weight of aluminum (Al) and the dry weight of silicon (Si) in said precipitated aluminosilicate.

Embodiment 11

The method of any preceding embodiment, wherein said structure-directing agent (R) is selected from the group consisting of cyclopentylamine, cyclohexylamine, cyclo-heptylamine, hexamethyleneimine (HMI), heptamethyleneimine, homopiperazine, and combinations thereof.

Embodiment 12

A process for converting feedstock comprising hydrocarbon compounds to conversion product which comprises contacting said feedstock at hydrocarbon compound conversion conditions with a catalyst composition made by the method of any one of embodiments 1 to 11.

Embodiment 13

The process of embodiment 12, wherein said feedstock comprises an alkylatable aromatic compound and an alkylating agent selected from the group consisting of olefins, alcohols, aldehydes, alkyl halides and combinations thereof, and said hydrocarbon compound conversion conditions include a temperature of from about 0° C. to about 500° C., a pressure from about 0.2 to about 250 atmospheres, a molar ratio of alkylatable aromatic compound to alkylating agent of from about 0.1:1 to about 50:1, and a feed weight hourly space velocity (WHSV) based on said alkylating agent of from about 0.1 to 500 hr$^{-1}$.

Embodiment 14

The process of embodiment 13, wherein said alkylatable aromatic compound is benzene, said olefin is ethylene, said conversion product comprises ethylbenzene, and said hydrocarbon compound conversion conditions include a temperature of from about 150° C. to about 300° C., a pressure of from about 20 to about 55 atmospheres, a weight hourly space velocity (WHSV) based on said ethylene alkylating agent of from about 0.1 to about 20 hr$^{-1}$, and a ratio of benzene to ethylene in a alkylation reactor of from about 0.5:1 to about 100:1 molar.

Embodiment 15

The process of embodiment 14, wherein said alkylatable aromatic compound is benzene, said olefin is propylene, said conversion product comprises cumene, and said hydrocarbon compound conversion conditions include a temperature of up to about 250° C., a pressure of about 250 atmospheres or less, a weight hourly space velocity (WHSV) based on propylene alkylating agent of from about 0.1 hr$^{-1}$ to about 250 hr$^{-1}$, and a ratio of benzene to propylene in a alkylation reactor of from about 0.5:1 to about 100:1 molar.

Non-limiting examples of the invention are described with reference to the following experiments. The crystallization time was to complete crystallization or a point when crystallization appeared to be complete or extremely slow. Unless otherwise specified, the reference to "Parts" is a reference to "parts on a molar basis."

EXAMPLES

The formulations of the synthesis mixtures used in the Examples are provided in Table 10, below, on a by Parts molar basis.

TABLE 10

| Component | | 1 Comparative (Molar Parts) | 2 Comparative (Molar Parts) | 3 Comparative (Molar Parts) | 4 (Molar Parts) | 5 (Molar Parts) | 6 (Molar Parts) | 7 (Molar Parts) | 8 (Molar Parts) |
|---|---|---|---|---|---|---|---|---|---|
| A | $H_2O$ | 360 | 286 | 229 | 370 | 294 | 234 | 234 | 366 |
| B | $Na_2O$ | 1.3 | 1.3 | 1.3 | 1.2 | 1.2 | 1.1 | 1.2 | 1.2 |
| C | $Al_2O_3$ | 1.0 | 1.0 | 1.0 | | | | | |
| D | $SiO_2$ (Sipernate 320) | 19.0 | 19.0 | 19.1 | | | | | |
| E | PAS | | | | 19.5 | 19.5 | 19.5 | 19.5 | 19.4 |
| F | SDA | 2.1 | 2.1 | 2.1 | 2.1 | 2.2 | 2.3 | 2.3 | 6.3 |
| | Molecular Sieve Seeds (Wt. %) | 1.0 | 1.0 | 1.0 | 2.0 | 1.0 | 1.0 | 1.0 | 2.0 |

The description and composition of the precipitated aluminosilicates (PAS) that were used in the Examples are set forth in Table 11, below.

TABLE 11

| | |
|---|---|
| $SiO_2/Al_2O_3$ (Molar Ratio) | 19-21 |
| $Na/SiO_2$ (Molar Ratio) | 0.10-0.15 |

The PAS was prepared as described in European Patent No. 0106552 for a homogeneous phase compound of a granular amorphous aluminosilicate.

The procedures for preparation and crystallization of the reaction mixtures in Examples 1 to 3, wherein sodium aluminate was the alumina source, were as follows. A mixture of solutions was made from A molar Parts of water, B molar Parts of a 50 wt. % NaOH solution, and C Parts of a 45% sodium aluminate solution (22% $Al_2O_3$, 19.5% $Na_2O$), and solution mixture was then charged to an autoclave reactor. This solution mixture was agitated at 60 rpm for 1 to 24 hours at ambient temperature. After which, D Parts $SiO_2$ (Ultrasil-VN3PM-Modified also called Sipernate 320) was added as the silica source. Molecular sieve seeds (MCM-56) were added as a drycake. The autoclave reactor was sealed and pressure tested. Afterwards, F Parts of structure-directing agent (SDA) as hexamethyleneimine (HMI as 100% organic) were charged. The autoclave reactor was heated to 160° C. with stirring at 50 rpm and crystallized long enough to form MCM-56. After crystallization was confirmed via X-ray diffraction (XRD), the autoclave reactor was cooled to 132° C. (270° F.) and SDA organics were removed. The reactor was cooled and the product discharged.

The procedures for preparation and crystallization of the synthesis mixtures in Examples 4 to 8, wherein the PAS was the alumina source as well as the silica source, were as follows. A solution made from A Parts of water, and B Parts of $Na_2O$, was charged to an autoclave reactor. The solution was agitated at 60 rpm for 1 to 24 hours at ambient temperature. After which, E Parts of PAS was added. Molecular sieve seeds (MCM-56) were added as a drycake. The autoclave reactor was sealed and pressure tested. Afterwards, F Parts of structure-directing agent (SDA) as hexamethyleneimine (HMI as 100% organic) were charged. The autoclave reactor was heated to 160° C. with stirring at 50 rpm and crystallized long enough to form MCM-56. After crystallization was confirmed via X-ray diffraction (XRD), the autoclave reactor was cooled to 132° C. (270° F.) and SDA organics were removed. The reactor was cooled and the product discharged.

The compositions in molar ratios of the synthesis mixtures which resulted for the Examples are shown in Table 12, below.

TABLE 12

| Composition (Molar Ratios) | 1 Comparative (Molar Parts) | 2 Comparative (Molar Parts) | 3 Comparative (Molar Parts) | 4 (Molar Parts) | 5 (Molar Parts) | 6 (Molar Parts) | 7 (Molar Parts) | 8 (Molar Parts) |
|---|---|---|---|---|---|---|---|---|
| $SiO_2/Al_2O_3$ | 19 | 19 | 19 | 19 | 19 | 19 | 19 | 19 |
| $H_2O/SiO_2$ | 19 | 15 | 12 | 19 | 15 | 12 | 12 | 19 |
| $OH^-/SiO_2$ | 0.12 | 0.12 | 0.12 | 0.12 | 0.12 | 0.11 | 0.12 | 0.12 |
| $Na/SiO_2$ | 0.14 | 0.14 | 0.14 | 0.12 | 0.12 | 0.11 | 0.12 | 0.12 |
| $N/SiO_2$ | 0.11 | 0.11 | 0.11 | 0.11 | 0.12 | 0.12 | 0.12 | 0.33 |
| Molecular Sieve Seeds (Wt. %) | 1.0 | 1.0 | 1.0 | 2.0 | 1.0 | 1.0 | 1.0 | 2.0 |

Figure 2:
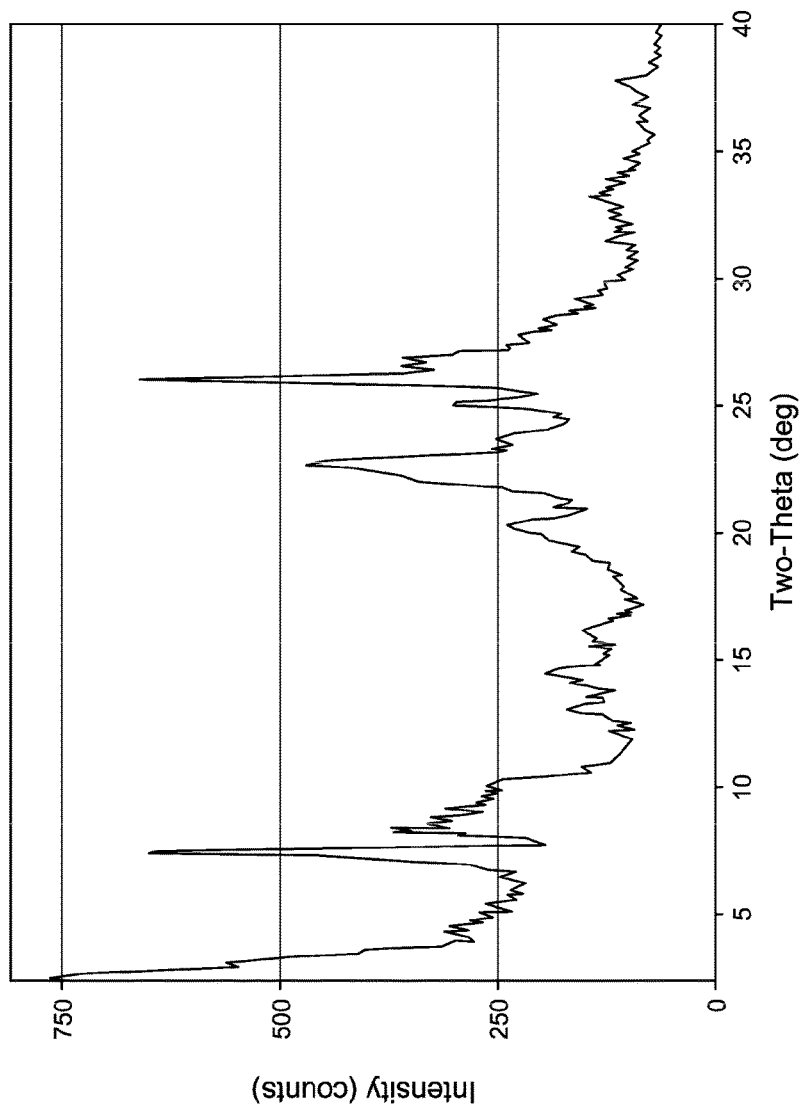
FIG. 2 shows the X-ray diffraction pattern of the as-synthesized MWW family molecular sieve material products of Example 2.
Figure 3:
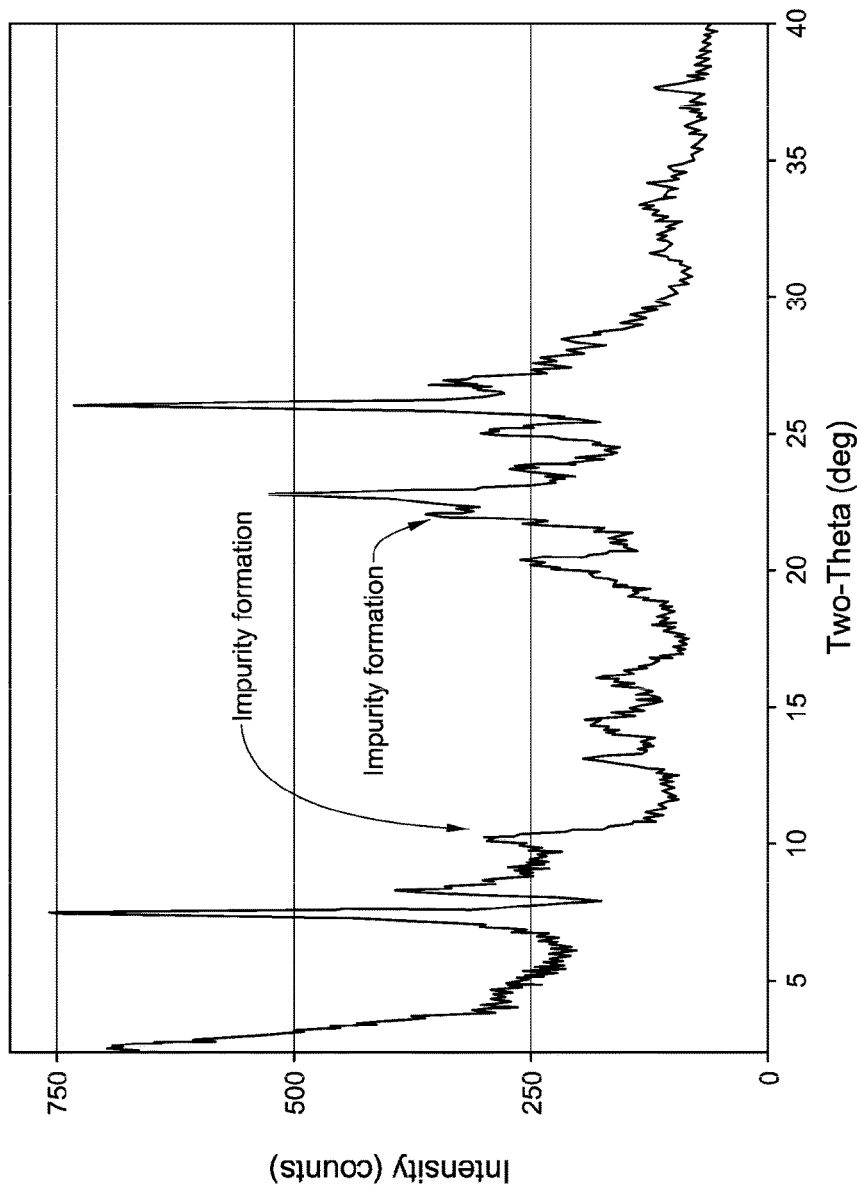
FIG. 3 shows the X-ray diffraction pattern of the as-synthesized MWW family molecular sieve material products of Example 3.
Figure 4:
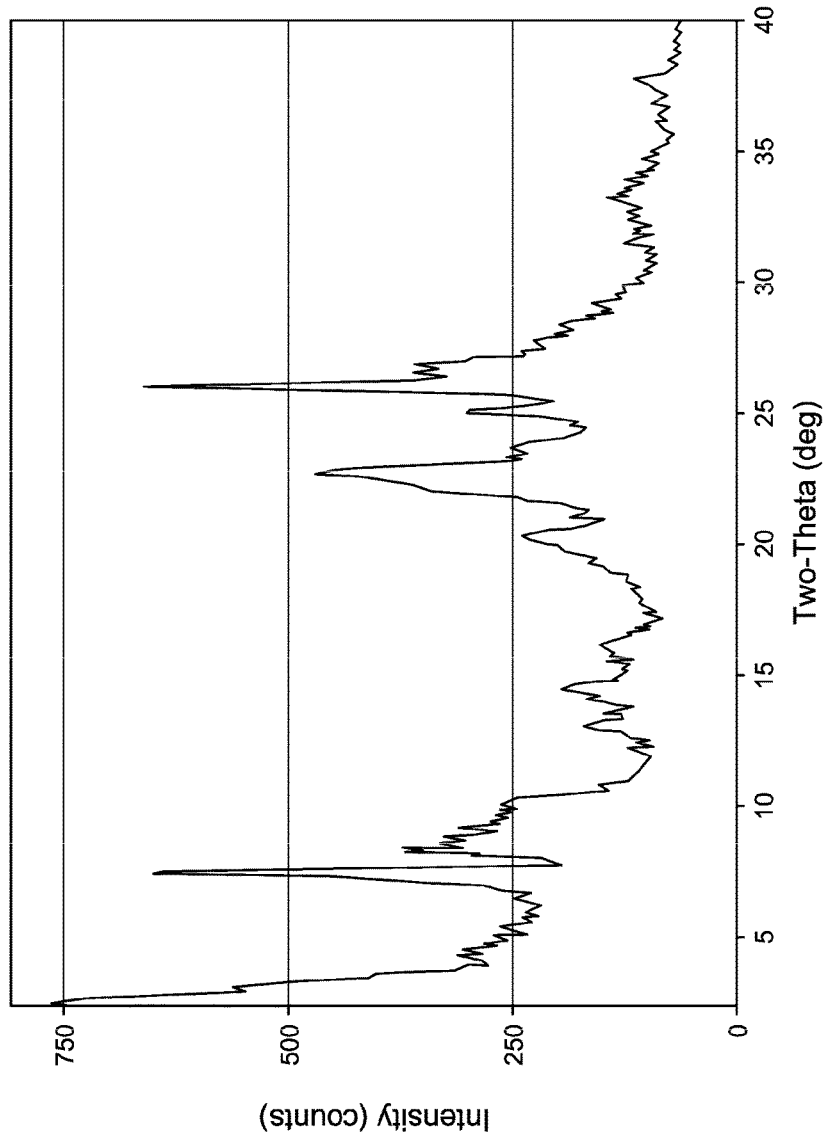
FIG. 4 shows the X-ray diffraction pattern of the as-synthesized MWW family molecular sieve material products of Example 4.
Figure 5:
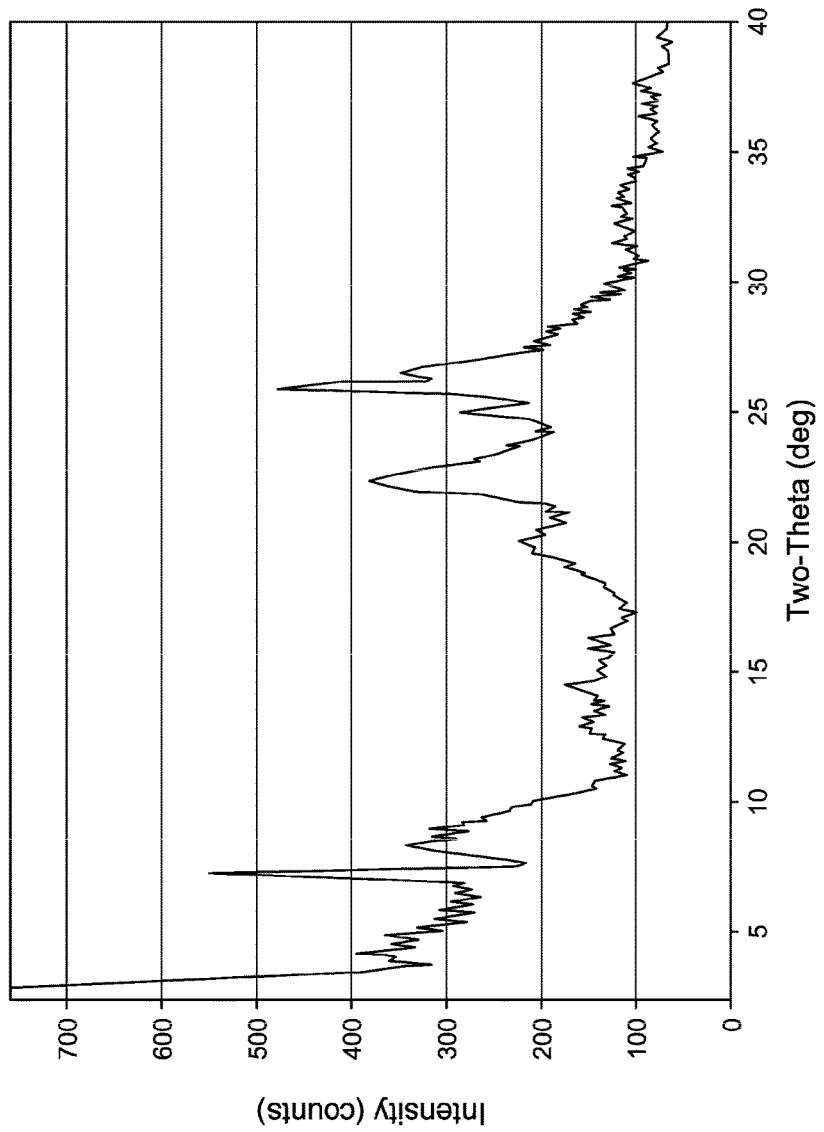
FIG. 5 shows the X-ray diffraction pattern of the as-synthesized MWW family molecular sieve material products of Example 5.
Figure 6:
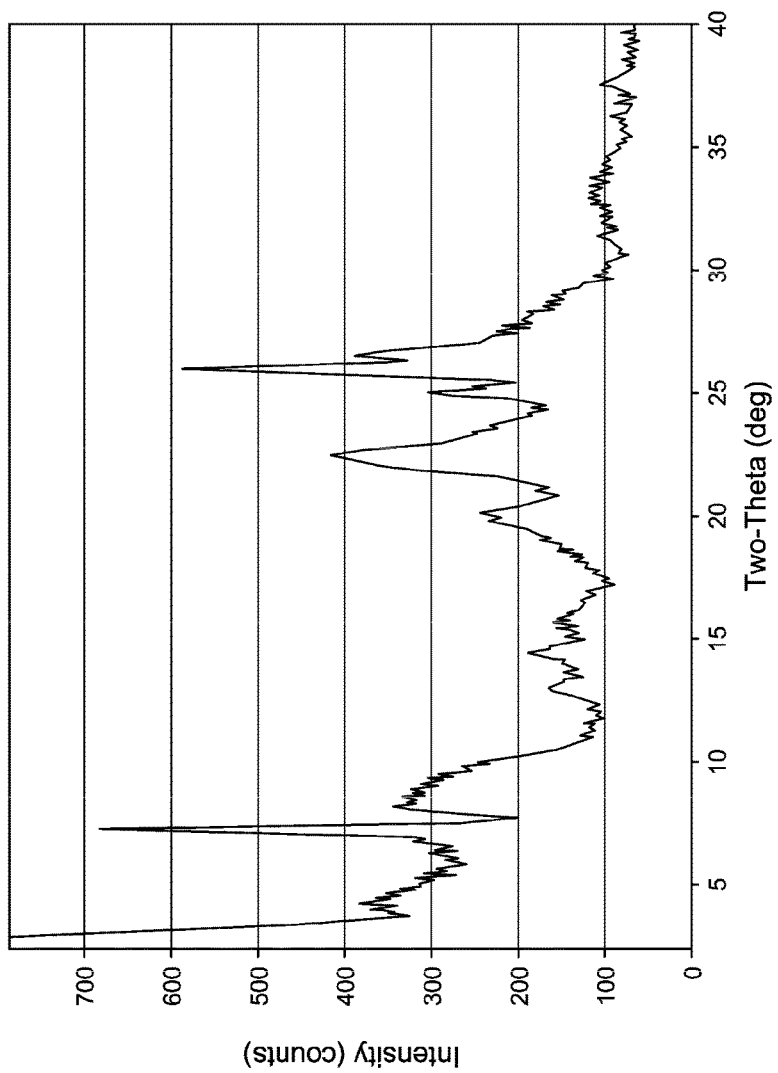
FIG. 6 shows the X-ray diffraction pattern of the as-synthesized MWW family molecular sieve material products of Example 6.
Figure 7:
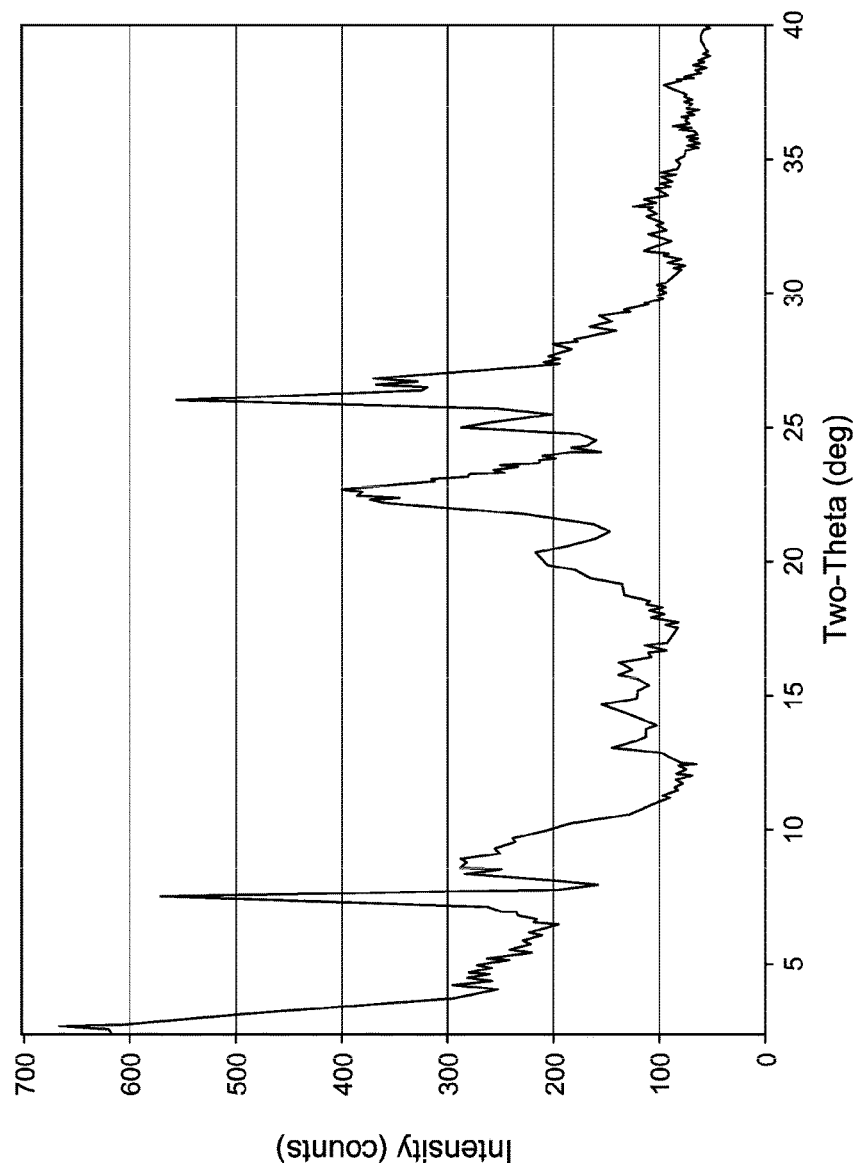
FIG. 7 shows the X-ray diffraction pattern of the as-synthesized MWW family molecular sieve material products of Example 7.
Figure 8:
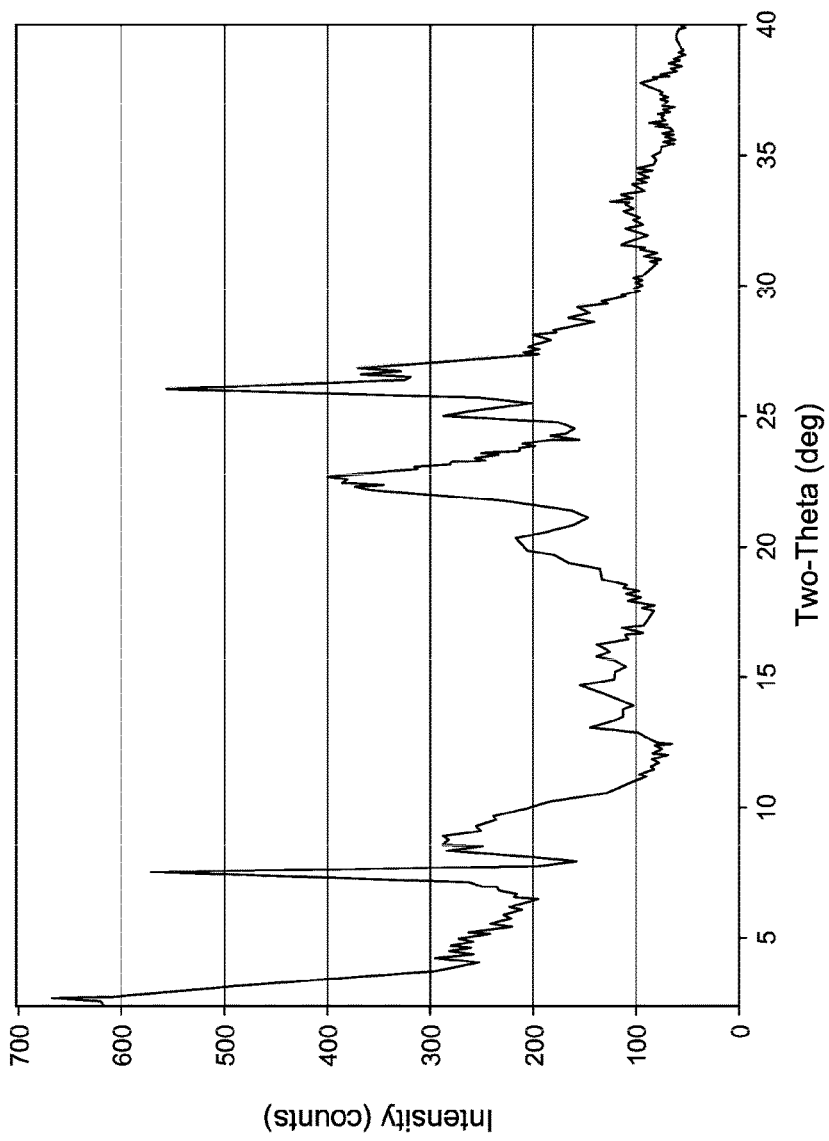
FIG. 8 shows the X-ray diffraction pattern of the as-synthesized MWW family molecular sieve material products of Example 8.

For the Examples, the crystallization time, temperature, stir rate and the result of the XRD of samples thereof are shown in Table 13, below. FIGS. 1 to 8 show the X-ray diffraction patterns of the as-synthesized MWW family molecular sieve material for Examples 1 to 8, respectively.

TABLE 13

| Crystallization Parameter | Example Number | | | | | | | |
|---|---|---|---|---|---|---|---|---|
| | 1 Comparative | 2 Comparative | 3 Comparative | 4 | 5 | 6 | 7 | 8 |
| Time (hrs) | 68 | 48 | 40 | 68 | 38 | 42 | 28 | 68 |
| Temp. (° C.) | 160 | 160 | 160 | 160 | 160 | 160 | 160 | 160 |
| Stir Rate (rpms) | 250 | 250 | 250 | 250 | 250 | 250 | 250 | 90 |
| XRD Result for Product | MCM-56 | MCM-56 | MCM-56 Contaminated with MCM-49 | MCM-56 | MCM-56 | MCM-56 | MCM-56 | MCM-49 |

In Examples 1-7, the use of PAS in the MWW family molecular sieve material synthesis of MCM-56 resulted in shorter crystallization times and higher throughput via lower $H_2O/SiO_2$ ratio. As can be seen, crystallization times were reduced to less than about 40 hours. Also, the $H_2O/SiO_2$ ratio was decreased to below 14 while still synthesizing the desired MCM-56 molecular sieve without appreciable impurity. Decreasing the $H_2O/SiO_2$ molar ratio in the formulations of the synthesis mixtures improves throughput by increasing the yield per batch. Conventional precipitated silica (such as Ultrasil or Sipernate 320) requires the addition of an aluminum source which often contains sodium (Na), for example, sodium aluminate). Using sodium aluminate limits the lower boundary of $Na/SiO_2$ ratio to about 0.14, depending upon the composition of the aluminum source. The alternative aluminum sources ($Al_2(SO_4)_3$) are acidic in nature and in order to obtain the target acidity, a substantial amount of NaOH is required. This further limits the lower boundary for sodium and does not allow one to obtain the targeted lower $OH/SiO_2$ and $Na/SiO_2$ ratios.

Example 7 was a repeat of Example 6 in which 50 wt. % NaOH was added to increase the $Na/SiO_2$ ratio to decrease crystallization time.

All patents, patent applications, test procedures, priority documents, articles, publications, manuals, and other documents cited herein are fully incorporated by reference to the extent such disclosure is not inconsistent with this invention and for all jurisdictions in which such incorporation is permitted.

When numerical lower limits and numerical upper limits are listed herein, ranges from any lower limit to any upper limit are contemplated.

While the illustrative embodiments of the invention have been described with particularity, it will be understood that various other modifications will be apparent to and may be readily made by those skilled in the art without departing from the spirit and scope of the invention. Accordingly, it is not intended that the scope of the claims appended hereto be limited to the examples and descriptions set forth herein but rather that the claims be construed as encompassing all the features of patentable novelty which reside in the present invention, including all features which would be treated as equivalents thereof by those skilled in the art to which the invention pertains.

We claim:

1. A method of making a MWW family molecular sieve material comprising the steps of:
    (a) preparing a solution comprising an alkali or an alkaline earth metal (M) cation and water,
    (b) preparing a precipitated aluminosilicate comprising a combined source of both aluminum (Al) and silicon (Si), said precipitated aluminosilicate having a composition in terms of mole ratios within the following ranges:

$SiO_2/Al_2O_3$=10 to 600;

(c) combining said solution and said precipitated aluminosilicate to form a reaction mixture having a composition in terms of mole ratios within the following ranges:

$H_2O/SiO_2$=5 to 15;

$OH^-/SiO_2$=0.001 to 2; and $M/SiO_2$=0.001 to 2;

(d) afterward adding an organic structure-directing agent (R) to said reaction mixture of step (c) so that it has a composition of structure-directing agent (R) in terms of mole ratios within the range:

$R/SiO_2$=0.001 to 0.5;

(e) crystallizing said reaction mixture of step (d) under crystallization conditions of a temperature of from about 90° C. to about 175° C. and a time for less than 90 hours to form a resulting mixture comprising crystals of said MWW family molecular sieve material and less than about 10 wt. % of impurity crystals having non-MWW framework structure based on the total weight of said MWW family molecular sieve material in said reaction mixture, as identified by X-ray diffraction; and
    (f) recovering at least a portion of said crystals of said MWW family molecular sieve material from said resulting mixture of step(e) as an as-synthesized MWW family molecular sieve material having an X-ray diffraction pattern including d-spacing maxima at 12.4±0.25, 6.9±0.15, 3.57±0.07 and 3.42±0.07 Angstroms.

2. The method of claim 1, wherein said as-synthesized MWW family molecular sieve material is thermally treated by heating at a temperature of from about 370° C. to about 925° C. for a time of from 1 minute to about 20 hours to form a calcined MWW family molecular sieve material.

3. The method of claim 1, wherein said composition of said reaction mixture in terms of mole ratios is within the following ranges:

$SiO_2/Al_2O_3$=15 to 50;

$H_2O/SiO_2$=5 to 15;

$OH^-/SiO_2$=0.01 to 0.3;

$M/SiO_2$=0.01 to 0.3;

$R/SiO_2$=0.01 to 0.5;

wherein said as-synthesized MWW family molecular sieve material has the X-ray diffraction pattern of as-synthesized MCM-22 molecular sieve shown in Table 1:

TABLE 1

| Interplanar d-Spacing (Angstroms) | Relative Intensity $I/I_0 \times 100$ |
|---|---|
| 13.53 ± 0.2 | m-vs |
| 12.38 ± 0.2 | m-vs |
| 11.13 ± 0.2 | w-s |
| 9.15 ± 0.15 | w-s |
| 6.89 ± 0.15 | w-m |
| 4.47 ± 0.1 | w-m |
| 3.95 ± 0.08 | w-vs |
| 3.56 ± 0.06 | w-m |
| 3.43 ± 0.06 | m-vs |
| 3.36 ± 0.05 | w-s. |

4. The method of claim 3, wherein said as-synthesized MCM-22 molecular sieve is thermally treated by heating at a temperature of from about 370° C. to about 925° C. for a time of from 1 minute to about 20 hours to form a calcined MCM-22 molecular sieve having the X-ray diffraction pattern shown in Table 2:

TABLE 2

| Interplanar d-Spacing (Angstroms) | Relative Intensity $I/I_0 \times 100$ |
|---|---|
| 30.0 ± 2.2 | w-m |
| 22.1 ± 1.3 | w. |

5. The method of claim 1, wherein said composition of said reaction mixture in terms of mole ratios is within the following ranges:

$SiO_2/Al_2O_3$=15 to 35;

$H_2O/SiO_2$=5 to 15;

$OH^-/SiO_2$=0.1 to 0.3;

$M/SiO_2$=0.08 to 0.3;

$R/SiO_2$=0.10 to 0.35;

wherein said as-synthesized MWW family molecular sieve material has the X-ray diffraction pattern of as-synthesized MCM-49 molecular sieve shown in Table 5:

TABLE 5

| Interplanar d-Spacing (Angstroms) | Relative Intensity $I/I_0 \times 100$ |
|---|---|
| 13.15 ± 0.26 | w-s* |
| 12.49 ± 0.24 | vs |
| 11.19 ± 0.22 | m-s |
| 6.43 ± 0.12 | w |
| 4.98 ± 0.10 | w |
| 4.69 ± 0.09 | w |

TABLE 5-continued

| Interplanar d-Spacing (Angstroms) | Relative Intensity $I/I_0 \times 100$ |
|---|---|
| 3.44 ± 0.07 | vs |
| 3.24 ± 0.06 | w. |

*shoulder

6. The method of claim 5, wherein said as-synthesized MCM-49 molecular sieve is thermally treated by heating at a temperature of from about 370° C. to about 925° C. for a time of from 1 minute to about 20 hours to form a calcined MCM-49 molecular sieve having the X-ray diffraction pattern shown in Table 6:

TABLE 6

| Interplanar d-Spacing (Angstroms) | Relative Intensity $I/I_0 \times 100$ |
|---|---|
| 12.41 ± 0.24 | vs |
| 11.10 ± 0.22 | s |
| 8.89 ± 0.17 | m-s |
| 6.89 ± 0.13 | w |
| 6.19 ± 0.12 | m |
| 6.01 ± 0.12 | w |
| 5.56 ± 0.11 | w |
| 4.96 ± 0.10 | w |
| 4.67 ± 0.09 | w |
| 4.59 ± 0.09 | w |
| 4.39 ± 0.09 | w |
| 4.12 ± 0.08 | w |
| 4.07 ± 0.08 | w-m |
| 3.92 ± 0.08 | w-m |
| 3.75 ± 0.07 | w-m |
| 3.57 ± 0.07 | w |
| 3.43 ± 0.07 | s-vs |
| 3.31 ± 0.06 | w |
| 3.21 ± 0.06 | w |
| 3.12 ± 0.06 | w |
| 3.07 ± 0.06 | w |
| 2.83 ± 0.05 | w |
| 2.78 ± 0.05 | w |
| 2.69 ± 0.05 | w |
| 2.47 ± 0.05 | w |
| 2.42 ± 0.05 | w |
| 2.38 ± 0.05 | w. |

7. The method of claim 1, wherein said composition of said reaction mixture, in terms of mole ratios, is within the following ranges:

$SiO_2/Al_2O_3$=15 to 25;

$H_2O/SiO_2$=5 to 15;

$OH^-/SiO_2$=0.10 to 0.15;

$M/SiO_2$=0.10 to 0.15;

$R/SiO_2$=0.1 to 0.2;

wherein said as-synthesized MWW family molecular sieve material has the X-ray diffraction pattern of as-synthesized MCM-56 molecular sieve shown in Table 7:

TABLE 7

| Interplanar d-Spacing (Angstroms) | Relative Intensity $I/I_0 \times 100$ |
|---|---|
| 12.4 ± 0.2 | vs |
| 9.9 ± 0.3 | m |
| 6.9 ± 0.1 | w |
| 6.4 ± 0.3 | w |

TABLE 7-continued

| Interplanar d-Spacing (Angstroms) | Relative Intensity $I/I_0 \times 100$ |
|---|---|
| 6.2 ± 0.1 | w |
| 3.57 ± 0.07 | m-s |
| 3.44 ± 0.07 | vs. |

8. The method of claim 7, wherein said as-synthesized MCM-56 molecular sieve is thermally treated by heating at a temperature of from about 370° C. to about 925° C. for a time of from 1 minute to about 20 hours to form a calcined MCM-56 molecular sieve having the X-ray diffraction pattern shown in Table 8:

TABLE 8

| Interplanar d-Spacing (Angstroms) | Relative Intensity $I/I_0 \times 100$ |
|---|---|
| 12.4 ± 0.2 | vs |
| 9.9 ± 0.3 | m |
| 6.9 ± 0.1 | w |
| 6.2 ± 0.1 | w |
| 3.55 ± 0.07 | m-s |
| 3.42 ± 0.07 | vs. |

9. The method of claim 1, wherein said alkali or said alkaline earth metal (M) cation is incorporated into the precipitated aluminosilicate.

10. The method of claim 1, wherein said reaction mixture of step (a) further comprises molecular sieve seed crystals in an amount from greater than or equal to 0.05 wt. % to less than or equal to 5 wt. %, based on the dry weight of said molecular sieve seed crystals divided by the sum of the dry weight of aluminum (Al) and the dry weight of silicon (Si) in said precipitated aluminosilicate.

11. The method of claim 10, wherein said molecular sieve seed crystals exhibit the X-ray diffraction pattern for an MWW family molecular sieve material.

12. The method of claim 11, wherein said MWW family molecular sieve material of said molecular sieve seed crystals is selected from the group consisting of MCM-22, MCM-36, MCM-49, MCM-56, ITQ-1, ITQ-2, ITQ-30, PSH-3, SSZ-25, ERB-1, EMM-10, EMM-10-P, EMM-11, EMM-12, EMM-13, UZM-8 and UZM-8HS.

13. The method of claim 1, wherein said crystallization conditions of crystallizing step (e) include crystallizing said reaction mixture for said time of from about 20 hours to about 75 hours.

14. The method of claim 1, wherein said organic structure-directing agent (R) is selected from the group consisting of cyclopentylamine, cyclohexylamine, cycloheptylamine, hexamethyleneimine (HMI), heptamethyleneimine, homopiperazine, and combinations thereof.

15. The method of claim 1, wherein said M is sodium, and said R comprises hexamethyleneimine (HMI).

16. The method of claim 1, wherein said impurity crystals having non-MWW framework structure is selected from the group consisting of ferrierite, kenyaite and mixtures thereof.

17. The method of claim 1, wherein said precipitated aluminosilicate is a granular amorphous aluminosilicate.

18. The method of claim 1, wherein said precipitated aluminosilicate is a precipitated sodium aluminosilicate.

* * * * *